US006865942B2

(12) United States Patent
Ghosh et al.

(10) Patent No.: US 6,865,942 B2
(45) Date of Patent: Mar. 15, 2005

(54) DEVICE FOR ESTIMATION OF BRINE DENSITY

(75) Inventors: Pushpito Kumar Ghosh, Bhavnagar (IN); Kishor Manmohandas Majeethia, Bhavnagar (IN); Mahesh Ramniklal Gandhi, Bhavnagar (IN); Jamnadas Naranbhai Parmar, Bhavnagar (IN); Ajoy Murlidhar Bhatt, Bhavnagar (IN); Shanti Amritlal Chauhan, Bhavnagar (IN); Puthoor Mohandas Vadakke, Bhavnagar (IN); Abdulhamid Usmanbhai Hamidini, Bhavnagar (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/393,405

(22) Filed: Mar. 20, 2003

(65) Prior Publication Data

US 2004/0182154 A1 Sep. 23, 2004

(51) Int. Cl.$^7$ .................................................. G01N 9/00
(52) U.S. Cl. .............................. 73/448; 73/444; 73/451
(58) Field of Search .......................... 73/440, 444, 448, 73/451, 453, 306, 322.5

(56) References Cited

U.S. PATENT DOCUMENTS

| | | | | |
|---|---|---|---|---|
| 1,074,039 A | * | 9/1913 | Berberich | 73/448 |
| 1,473,309 A | * | 11/1923 | Moeller | 73/448 |
| 1,550,412 A | * | 8/1925 | Albrecht et al. | 73/448 |
| 1,610,606 A | * | 12/1926 | Hiergesell | 73/448 |
| 1,935,703 A | | 11/1933 | Fairchild et al. | 265/45 |
| 2,067,914 A | | 1/1937 | Godfrey | 265/45 |
| 2,221,913 A | * | 11/1940 | Edelmann | 73/448 |
| 3,460,395 A | * | 8/1969 | Shaw | 73/440 |
| 3,677,356 A | * | 7/1972 | Goodwin | 177/190 |
| 4,338,817 A | * | 7/1982 | Callahan | 73/448 |
| 2002/0170354 A1 | * | 11/2002 | Monsrud et al. | 73/305 |
| 2002/0170861 A1 | | 11/2002 | Monsrud et al. | 210/744 |

FOREIGN PATENT DOCUMENTS

EP          0916303          5/1999

* cited by examiner

*Primary Examiner*—Helen Kwok
(74) *Attorney, Agent, or Firm*—Ladas & Parry LLP

(57) ABSTRACT

The present invention relates to a novel device that enables a person to gauge the brine density in solar salt works from afar without recourse to sampling of the brine. The device—which can be considered as an improvisation over the conventional laboratory type Baume meter—an be placed directly in the salt pa. The device remains sunk, and therefore invisible, until the desired density of brine is approached. Thereafter it gradually floats up and becomes visible from afar. From appropriate markings on the rod connected to the top end of the device, it can be gauged whether the brine is yet to attain the desired density, or has attained the desired density range, or has exceeded the desired density range. The device is resistant to corrosion and able to combat extreme weather conditions prevailing in solar salt works. The control of brine density from afar helps eliminate the need for frequent sampling of brine for density measurement that would make adherence to the optimum process of salt production easier. The methodology can be extended to production of other marine chemicals such as carnallite and kainite.

20 Claims, 3 Drawing Sheets

DEVICE FOR ESTIMATION OF BRINE DENSITY

FIELD OF THE INVENTION

The present invention relates to a device for estimation of brine density. More particularly, the present invention relates to a device for the estimation of brine density in solar salt works from afar.

In the field of salt technology this invention relates to the design and fabrication of a device that enables producers of salt and marine chemicals in solar salt works to sense the density of brine in salt pans from afar and which can be suitably modified to make it sensitive to select ranges of brine density useful in production of solar salt and other marine chemicals.

BACKGROUND OF THE INVENTION

In "Sodium chloride, The Production and Properties of Salt and Brine", edited by Dale W. Kaufmann, the density at which brine is charged and discharged in salt pans has a profound effect on the quality and yield of solar salt. If the crystalliser is charged before the desired density of brine is attained, the salt can be contaminated with higher amounts of gypsum. On the other hand, if discharge of brine after salt crystallization is delayed, the salt will have a higher content of magnesium sulphate impurity. If charging of brine into the crystallizer is delayed beyond the optimum brine density range for charging and it is discharged ahead of the optimum density range for discharge, then the yield of salt will get adversely affected. The purity of salt is of profound importance in many industrial applications such as chloralkali and soda ash manufacture. The price of industrial salt is strongly linked to its purity. The commonest industrial method of measuring brine density involves the use of hydrometer/Baume meter. The main disadvantage of the presently available devices is that they are laboratory-type instruments that work when a sample of the brine is made available, e.g., in a beaker. For this, one has to go every time up to the condenser/crystallizer and collect the brine sample and measure the density. Solar salt works are characteristically large in area and sampling of brine is a cumbersome process. As a result, frequent monitoring of brine density becomes problematic and there can be greater variation in the quality of salt produced due to inadequate sampling. Any device that alleviates this problem is, therefore, desirable. This is all the more so keeping in mind that actual field workers in many developing countries are illiterate and may not appreciate the value of stringent process control.

Another method of measuring the brine density is by the use of specific gravity bottle. This allows accurate estimation of brine density but suffers from the same drawback mentioned above, namely the need to physically sample the brine.

To overcome the disadvantages of the presently available devices and methods for the measurement of brine density in solar salt works to produce salt of desired specifications, an improvised version of the Baume meter is developed that can be placed in the salt pan itself and allows producers of salt to have an indication of the brine density from afar.

OBJECTS OF THE INVENTION

The main object of the invention is to provide a cost-effective device for the estimation of brine density in a medium from afar based on the principle of buoyancy that allows brine density to be monitored from a distance with a minimum precision of ±0.50° Be' and thereby eliminates the need for physical sampling of the brine for measurement of its density.

Another object of the invention is to provide a device for the estimation of brine density that is capable of easy adaptation to different ranges of density.

Yet another object of the invention is to provide a durable device for estimation of brine density that is resistant to corrosion and weathering effects.

Yet another object of the invention is to provide a device for the estimation of brine density that is accurate, is not subject to salt encrustation, and precise in its readings.

Yet another object of the invention is to provide a device for estimation of brine density in a medium that is easily visible even when there is minimum illumination such as at night.

Yet another object is to improve the adherence to process control during salt production by simplifying the operation of density monitoring.

Yet another object is to reduce the variation in the quality of salt and marine chemicals produced in solar salt works.

SUMMARY OF THE INVENTION

Accordingly the present invention provides a device for the estimation of brine density comprising (a) a semispherical main body means, (b) a rod connected to the semispherical body at the top thereof to provide a visible indication of brine density, (c) a weight means attached to the bottom of main body means for weight adjustment, (d) a hollow connecting means for connecting the rod and the weight means to the main body means and to enable insertion of additional compensating weights if desired for fine adjustment of weight of the device.

In one embodiment of the invention, the semispherical main body means comprises of a semispherical FRP body.

In an embodiment of the invention, the weight means comprises of a FRP coated disc.

In yet another embodiment of the invention, the connecting means comprises of a hollow bush with threaded ends and respective nuts to enable connection of the rod and weight means to the main body means.

In another one embodiment of the invention, the materials used for construction of the device are fiber—reinforced plastic and stainless steel for high tolerance to corrosion and large temperature variations.

In another embodiment of the invention, the volume of the device ranges from 2.500–3.500 liters.

In yet another embodiment of the invention, the device is calibrated in different density ranges of brine, more particularly, though not exclusively in the ranges of 16–17° Be', 24.5° –25.5° Be', and 28.5–29.5° Be'.

In a further embodiment of the invention, the stainless steel weight disk attached to the FRP body has a weight in the range of 0.500–1.500 kilogram and is fixed in accordance with the volume of the device and the brine density range where maximum sensitivity is sought.

In a further embodiment of the invention, the stainless steel rod attached to the top of the main body is provided with a plurality of markings at varying levels thereon, in order to indicate whether the desired brine density is yet to be achieved or whether it has been achieved or whether it has been exceeded.

In a further embodiment of the invention, the markings comprise of different colours.

In a further embodiment of the invention, the stainless steel rod attached to the top of the main body can optionally be painted with fluorescent paint or strapped with florescent tape for visibility when the surroundings are poorly illuminated.

BRIEF DESCRIPTION OF THE ACCOMPANYING DRAWINGS

DETAILED DESCRIPTION OF THE INVENTION

The present invention provides a novel device based on the principle of buoyancy for monitoring the brine density in solar salt works from afar for simpler process control which, in turn, facilitates strict adherence to process control and leads to reduced variations in quality of salt produced. The novelty of the invention resides in the (i) the appreciation of the need for a device that can be placed directly in the salt pan so as to enable the density of brine to be monitored from afar and (ii) putting desire into practice through the fabrication of a suitable device. The device operates on the principle of buoyancy—does the conventional Baume meter—but has the advantage of being a field unit that eliminates the need for sampling of brine. The fact that such a device has so far not been available for monitoring brine density from a distance despite its obvious utility is evidence of the non-obviousness of the invention.

Principle of the Working of the Device (BUOYANCY)

If a body is floating in a fluid and is at rest, it will be in equilibrium in a vertical plane. Then total upward force must be equal to the total downward force. This is true whether the body be immersed in a liquid or a gas. The downward force on the body will be due to gravity, whilst the upward force will be due to resultant upward pressure of the fluid in which the body is floating. This resultant upward pressure is known as the buoyancy.

Figure 1:
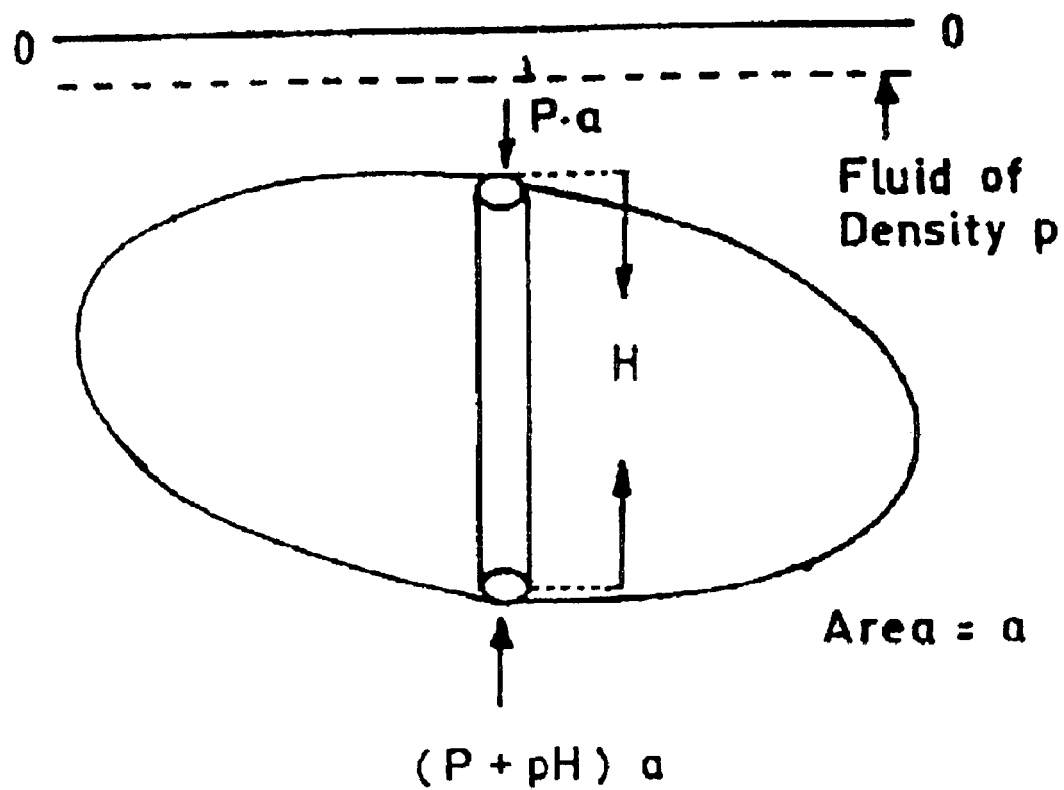
FIG. 1 illustrates the well-known principle of buoyancy on which the device of the invention works.
Figure 2:
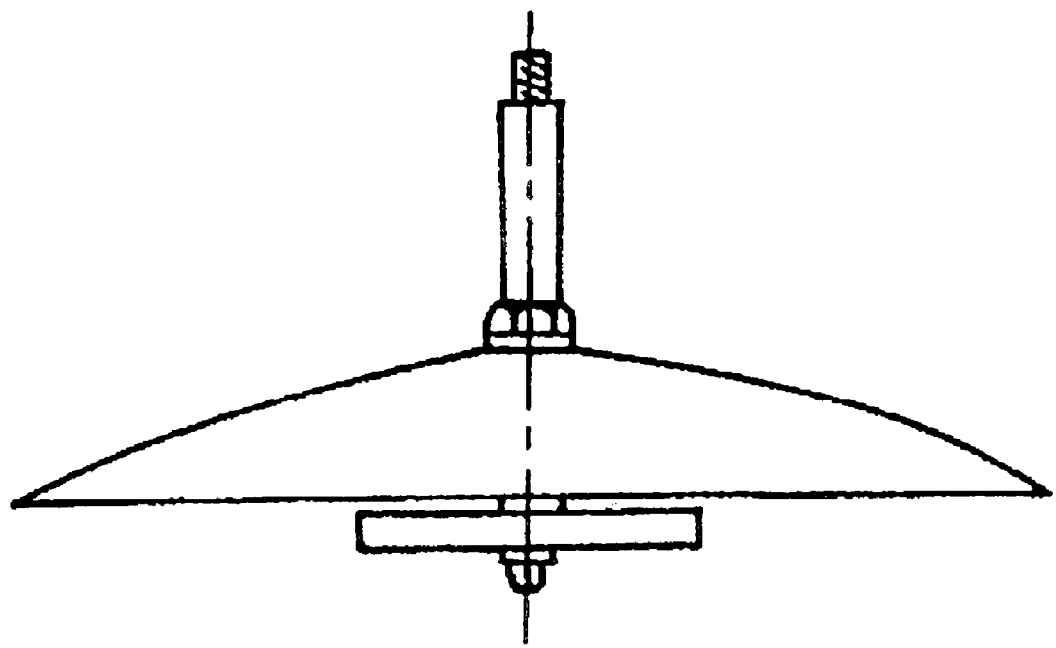
FIG. 2 shows the assembled device of the invention as a whole

As shown in FIG. 1, 0—0 is the surface of the fluid. Consider a vertical infinitesimally small element of a conduit of height H and cross-sectional area, a. Let P be the pressure of the fluid on the upper end of element. Then the pressure on the lower end of the element will be P+$\rho$H, the additional value $\rho$H being due to the additional depth of fluid of density $\rho$.

Total downward force of fluid on the element=P.a (1)

Total upward thrust of fluid on the element=(P+$\rho$H)a (2)

Resultant Upward thrust of a fluid on the element=(2)−(1)=$\rho$.H.a (3)

But H.a=Volume of the element (4)

Therefore, resultant upward thrust=$\rho$×volume of the element=weight of fluid displaced by the element. If the whole body is imagined to be made up of similar vertical elements, it follows that the total resultant upward thrust of the fluid will equal the weight of the fluid displaced by the body.

Density Measurement:

A body of constant volume, V, and weight, W, put into a fluid of density, $\rho$ will sink if W>V$\rho$ and will float if W<V$\rho$. Thus by knowing the volume of the fluid displaced and density of the fluid, the weight of the body can be adjusted so as to either float or sink in the fluid.

The device preferably comprises of a hollow fiber reinforced plastic (FRP) body of diameter ranging from 30–40 cm, bottom weight consisting of high density metal coated with FRP material, and stainless steel rod at the top of the disc coated with 3-color label that is visible to the naked eye and even more easily visible through a binocular, and optionally strapped with fluorescent tape for easy visibility in poorly illuminated conditions. Such device is put in a pond containing the brine for concentration. The device floats up to the calibrated level on attaining the desired brine density which can therefore be monitored from a distance and facilitate decision making on brine management in the solar salt works.

The material of construction of the device is compatible with any brine of any concentration, and is tolerant to the corrosive property of brine and the large temperature variations in the solar salt works that are typically set up in semi-arid regions. The materials used for construction of the device are fiber reinforced plastic and stainless steel. The configuration of the device is so made as to minimize accumulation of salts that might alter the precision of the device.

Figure 3:
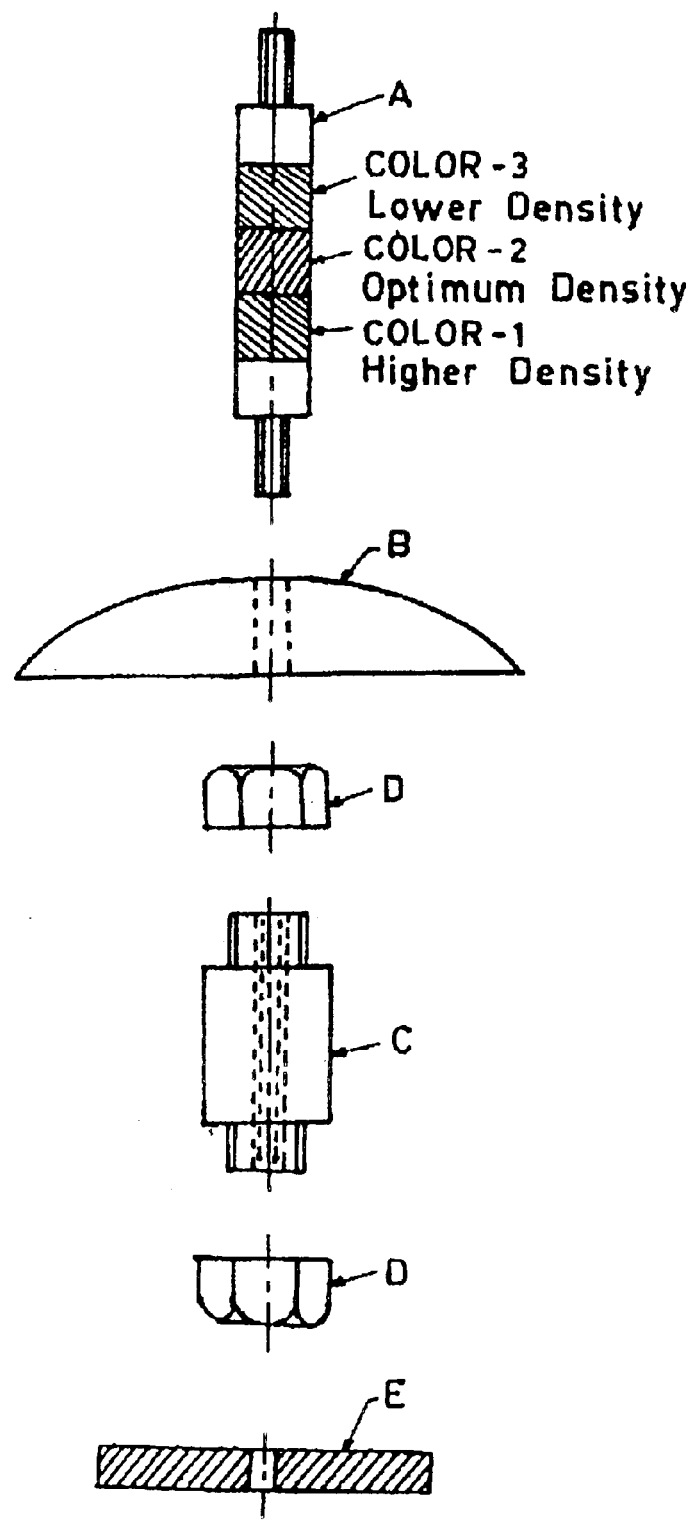
FIG. 3 shows various parts constituting the device

Various parts depicted in FIG. 3 are:

A—Stainless steel rod with three different color markings to differentiate<optimum density range, optimum density range, and >optimum density range of brine. The rod can optionally be coated with fluorescent paint or strapped with fluorescent tape for easy visibility under poorly illuminated conditions.

B—Semispherical body made out of Fiber Reinforced Plastic

C—Stainless steel bush with inbuilt thread to hold rod (A) and weight disc (E), arrangement for putting small weight for fine tuning D—Stainless steel nuts for fixing rod (A) at top and disc (E) at the bottom of body (B)

E—Stainless steel disc with FRP coating for weight adjustment

The stainless steel weight (E) put at the bottom of the body (B), ranges from 0.500–1.500 kilogram. It is fixed in accordance with the volume of the device-which ranges from 2.500–3.500 liters—and the brine density range where maximum sensitivity is sought.

The device is calibrated in different density ranges of brine. i.e., 16–17° Be', 24.5°–25.5° Be', and 28.5–29.5° Be'. The top stainless steel rod, A, is marked with three different colors where exposure of the middle color indicates attainment of the desired density range of brine. A binocular can be used for improved visibility of markings on the rod, A. The rod, A, can be strapped with florescent tape for visibility when the surroundings are poorly illuminated, as during nighttime.

The components of the device preferably are: (i) Stainless steel rod where different portions of the rod are coated with paint of different colors or optionally coated with florescent paint or strapped with fluorescent tape (A), (ii) FRP body (B), (iii) Stainless steel bush (C), (iv) stainless steel nuts to fix rod (A) and weight disc (E) to the main body (B), (v) Stainless steel disc with FRP coating for weight adjustment (E)

i. Stainless steel rod (A): The rod is made of S.S. 316/S.S. 416 and is threaded at top and bottom end. It is fixed to the top part of the float into the threaded bush embedded in the float body. The length of the rod is about 10–15 cm. The rod is visible from a distance when the device is floating in the high-density brine and is not visible when it sinks in the low density brine in a typical range of density for which it is calibrated. Different color portions on the rod allow for greater precision of density measurement, where the middle color represents optimum density range. The rod can be coated with fluorescent paint or strapped with fluorescent tape to make it visible in the dark.

ii. Semispherical Body (B): The float body is a hollow semi-spherical body with flat bottom made up of FRP with bright color that can begin to be seen when the desired density is being approached and which can be easily identified in case the device needs to be taken out from the salt pan. The FRP is cast on a hollow S.S. Bush provided with threads on both sides.

iii. Stainless steel hollow bush (C): The hollow bush is made of S.S 316 with both the ends threaded. The threaded part of the bush is used for fixing the rod (A) at the top and weight disc (E) at the bottom of the semispherical body (B). Small weights in the form of metal balls can be inserted in the bush for fine adjustment of the weight of the device.

iv. Stainless steel nuts (D): The nuts help fixing of rod (A) and weight disc (E) to the device.

v. Disc for weight adjustment (E): The disc is made out of S.S. 316 with FRP coating and its weight is determined based on the volume of the device and the density range of the brine.

Prior art does not contain any report on the device of the invention which is an improvised version of the Baume meter and which helps brine density to be monitored from afar and even in darkness. The unit is simple, robust and cost-effective and density can be monitored even by a non-specialist. The following examples are illustrative and provide the functioning of the device and steps involved in monitoring the brine density in salt works using the device of the invention. These examples should not be construed as limiting the scope of the invention.

EXAMPLE-1

A semispherical body of volume 2.70 liters faith a flat bottom made of fibre reinforced plastic was fabricated and the weight of the device including rod (A), FRP body (B), bush (C) and nuts (D) was 2.23 kg. An additional weight of 1.042 kg was added by attaching disc (E) to the float body to make the total weight to 3.28 kg with additional weight for fine adjustment. The device was calibrated by testing it in brine in the density range of 24.5 Be' to 25.5° Be'. The device sinks completely in 24.5° Be' and it floats at 25.5° Be', as expected based on calculations. The device remains erect indicating perfect balance.

EXAMPLE-2

A semispherical body of volume 2.70 liters with a flat bottom made of fibre reinforced plastic was fabricated and the weight of the device including rod (A), FRP body (B), bush (C) and nuts (D) was 2.230 kg. An additional weight of 0.82 kg. was added by attaching disc (E) to the float body with fine adjustment of weight to make the total weight to 3.08 kg. The device was calibrated by testing it in brine in the density range of 16° Be' to 17° Be'. The device sinks completely in 16° Be' and it floats at 17' Be', as expected based on calculations. The device remains erect indicating perfect balance.

EXAMPLE-3

A semispherical body of volume 2.70 liters with a flat bottom made of fiber reinforced plastic was fabricated and the weight of the device including rod (A), FRP body (B), bush (C) and nuts (D) was 2.23 kg. An additional weight of 1.14 kg was added by attaching disc (E) to the float body with fine adjustment to make the total weight to 3.375 kg. The device was calibrated by testing it in brine in the density range of 28° Be' to 29° Be' The device was observed to sink completely in 28° Be' and to float at 29° Be', as expected based on calculations. The device remains erect indicating perfect balance.

EXAMPLE-4

Several numbers of the device of example 1 were installed in various salt fields belonging to a major Indian producer of industrial grade solar salt from seawater. Consistent charging of the crystallizer at 25.6° Be' reduced the percentage of off-spec (salt with Ca impurity>0.20% was considered to be off spec) product considerably and the salt produced had calcium impurity typically in the range of 0.16–0.18%.

We claim:

1. A device for the estimation of brine density comprising the following components (a) a semispherical main body, (b) a rod connected to the semispherical body at the top thereof to provide a visible indication of brine density, (c) a weight means attached to the bottom of the main body for weight adjustment, (d) a hollow connecting means for connecting the rod and the weight means to the main body and to enable insertion of additional compensating weights if desired for fine adjustment of weight of the device.

2. A device as claimed in claim 1 wherein the semispherical main body comprises a semispherical fiber-reinforced plastic body.

3. A device as claimed in claim 1 wherein the weight means comprises a fiber-reinforced plastic coated disc.

4. A device as claimed in claim 1 wherein the connecting means comprises of a hollow brush with threaded ends and respective nuts to enable connection of the rod and the weight means to the main body.

5. A device as claimed in claim 1 wherein the components are fiber-reinforced plastic and stainless steel for high tolerance to corrosion and large temperature variations.

6. A device as claimed in claim 1 wherein a volume of the device ranges from 2.500–3.500 liters.

7. A device as claimed in claim 1 wherein the device is calibrated in different density ranges of brine.

8. A device as claimed in claim 7 wherein the device is calibrated in ranges selected from the group consisting of 16–17° Be', 24.5°–25.5° Be', and 28.5–29.5° Be'.

9. A device as claimed in claim 1 wherein the weight means attached to the main body has a weight in the range of 0.500–1.500 kilogram and is fixed in accordance with the volume of the device and brine density range where maximum sensitivity is sought.

10. A device as claimed in claim 1 wherein the rod attached to the top of the main body is provided with a plurality of markings at varying levels thereon, to indicate whether a desired brine density is yet to be achieved or whether the desired brine density has been achieved or whether the desired brine density has been exceeded.

11. A device as claimed in claim 10 wherein the markings comprise of different colors.

12. A device as claimed in claim 10 wherein the rod attached to the top of the main body is provided with visibility enhancing means for visibility in poor illumination.

13. A device as claimed in claim 12 wherein the visibility enhancing means comprises fluorescent paint or fluorescent tape.

14. A device for estimating brine density comprising (i) a semispherical main body; (ii) a rod connected to the semispherical main body at a top thereof; (iii) a weight adjustment element; (iv) means for connecting the rod and the weight adjustment element to the main body and for holding an additional weight adjustment element; said semispherical main body having a volume and said device having a weight that are calibrated such that (a) the device floats in brine having a first density with at least a marked portion of the rod being visible above a surface of the brine having the first density and (b) the device sinks completely in brine having a second density that is 1.0° Be' lower than the first density whereby the rod is not visible above the surface of the brine having the second density.

15. A device as claimed in claim 14, wherein the first density is selected from the group consisting of 17° Be', 25.5° Be' and 29.5° Be'.

16. A device as claimed in claim 15, wherein the marked portion of the rod comprises a color that is different from a color or colors of a remainder of the rod.

17. A device as claimed in claim 16, wherein the rod comprises visibility enhancing means for making the marked portion rod visible in poor illumination.

18. A device as claimed in claim 17, wherein the visibility enhancing means comprises fluorescent paint or flourescent tape.

19. A device as claimed in claim 18, wherein the means for connecting connects the rod and the weight adjustment element to the main body with the main body disposed between the rod and the weight adjustment element the device further comprising an additional weight adjustment element in the means for connecting.

20. A method of estimating brine density comprising the steps of:

(a) providing the, device of claim 14;
(b) placing the device in brine having a density that is at least 1.0° Be' below said first density; and
(c) monitoring the device to determine if the density of the brine has increased to said first density by a visual inspection to ascertain if the marked portion of the rod is above the surface of the brine without physically sampling the brine.

* * * * *